(12) United States Patent
O'Lenick, Jr.

(10) Patent No.: US 8,003,087 B1
(45) Date of Patent: Aug. 23, 2011

(54) MULTIPHILLIC SILICONE POLYSORBATE SOFTENERS

(75) Inventor: Anthony J. O'Lenick, Jr., Dacula, GA (US)

(73) Assignee: Siltech LLC, Lawrenceville, GA (US)

( * ) Notice: Subject to any disclaimer, the term of this patent is extended or adjusted under 35 U.S.C. 154(b) by 971 days.

(21) Appl. No.: 11/977,634

(22) Filed: Oct. 25, 2007

(51) Int. Cl.
*A61Q 5/12* (2006.01)
(52) U.S. Cl. ...................................... 424/70.12; 528/26
(58) Field of Classification Search ........................ None
See application file for complete search history.

(56) References Cited

U.S. PATENT DOCUMENTS 6,239,290 B1   5/2001   Buffa et al.
7,452,382 B1 * 11/2008   LaVay et al. ................. 8/115.51

* cited by examiner

*Primary Examiner* — Jyothsna Venkat

(57) ABSTRACT

The present invention is directed to a class of polyesters that have dimethicone copolyol and polysorbate units linked by the reaction of their hydroxyl groups into a polyester by the esterification reaction with succinic anhydride. The polymers and a contribute softness, lubricity and antistatic properties when applied to hair, skin, textile fiber and paper.

16 Claims, No Drawings

MULTIPHILLIC SILICONE POLYSORBATE SOFTENERS

RELATED APPLICATIONS

None

FEDERAL SPONSORSHIP

None

FIELD OF THE INVENTION

The present invention is directed to a class of polyesters that have dimethicone copolyol and polysorbate units linked by the reaction of their hydroxyl groups into a polyester by the esterification reaction with succinic anhydride. The polymers and a contribute softness, lubricity and antistatic properties when applied to hair, skin, textile fiber and paper. These water-loving materials are referred to as multiphillic, that is compounds made up of at least three groups that in pure form are insoluble in each other. Multiphillic is a coined contraction for multiple amphillic, and literally means having more than two groups, which are mutually insoluble in each other. An example of non-limiting groups that are mutually insoluble in each other include water, oil, silicone and fluoro compounds. When combined in a molecule having at least three of these groups a new class of surfactants is achieved. Proper selection of the chemistry of each group results in the ability to custom tailor molecules for delivery from aqueous solution onto substrate I surprisingly effective manners. A very specific group of multiphillic materials are the products of the current invention and are very effective surface active agents, not only lowering surface tension of water, but also providing softness, antistatic and wetting properties. The presence of the fatty, silicone and water-soluble groups provides unique and heretofore unobtainable properties on a variety of substrates.

BACKGROUND OF THE INVENTION

Surfactants are a class of materials that have two groups present in the same molecule that are insoluble in each other in pure form, For example, oil is insoluble in water, but when an oil soluble group is on a molecule with a water soluble group surface active agents or surfactants result.

The literature is full of surface active agents that have a fatty hydrophobe and a water soluble hydrophilic portion. Polysorbates arte one class.

Wikiopedia defines polysorbate as an oily liquid. It is a class of emulsifiers used in some pharmaceuticals and food preparation. It is often used in cosmetics to solubilise essential oils into water based products. Polysorbates are derived from PEG-ylated sorbitan (a derivative of sorbitol) esterified with fatty acids. Surfactants that are esters of plain (non-PEG-ylated) sorbitan with fatty acids are usually referred to by the name Span U.S. Pat. No. 4,297,290 to Stockberger issued Oct. 27, 1981 teaches that sorbitan fatty acid esters can be prepared by forming anhydro sorbitol (a mixture of sorbitans, isosorbide, and unreacted sorbitol) by acid-catalyzed anhydrization, then reacting the resulting anhydro sorbitol with a fatty acid in the presence of a base at a temperature not exceeding about 215° C. Use of temperatures not over 215° C. results in products having substantially less color than those obtained at higher temperatures.

Polysorbates are emulsifiers, but are sticky on the hair and skin and do not provide appreciable softness, conditioning or antistatic properties.

Silicone, is another group of compounds that in pure form are insoluble in oil and in water, placing them together in a molecule results in a amphillic material. Such materials are referred to as dimethicone copolyol.

U.S. Pat. No. 6,162,888 to Lee et all, incorporated herein by reference. This invention relates to a method of making a silicone polyether comprising (I) reacting a mixture comprising an olefin functional polyether, an organohydrogensiloxane, and a homogeneous transition metal hydrosilylation catalyst, and (II) subjecting the product of (I) to hydrogen gas. The method of this invention reduces the amount of olefinic species present, which are precursors to odorous compounds. This approach has several drawbacks. While the hydrogenation does lower the amount of vinyl groups present, the resulting saturated compound has very little difference in boiling point and is not an improvement in odor.

We have surprisingly found that tripolymers of alkyl polysorbates, dimethicone copolyol and succinic anhydride when reacted in the proper ratio using a specific process, give polymers with unique properties, providing wetting, softness hydrophilicity and durability, heretofore unachievable.

THE INVENTION

Objective of The Invention

It is the object of the invention to provide materials, which provide outstanding softness, antistatic properties and conditioning properties to a variety of substrates including hair, skin, textile fiber and paper.

Another object of this invention is to provide a unique two step process to optimize the structure of the polymer. As will become clear, the process includes a first step of reacting a dimethicone copolyol with succinic anhydride at a lower temperature to form a carboxyl ester, followed by adding polysorbate and heating to high temperature.

SUMMARY OF THE INVENTION

The present invention is directed to a polyester multiphillic molecule that comprises a two-step reaction. In the first step reaction includes the ring opening reaction of polysorbate with succinic anhydride, which results in a carboxy ester compound. This first reaction is conducted at a temperature of no higher than 110° C. The resulting compound has an acid value that indicates very little polyester has formed. The reactions are conducted in tandem fashion, with an excess of hydroxyl groups. In the first step only a low percentage of the dimethicone copolyol hydroxyl groups are reacted, leaving the remainder of the groups free.

In a subsequent step, a dimethicone copolyol is added, an esterification catalyst is added and the temperature is increased to between 150 and 210° C. An esterification catalyst can be added to accelerate the reaction, but the excess of hydroxyl groups manes this unnecessary. This high temperature results in the carboxy group on the polysorbate to react with additional groups having hydroxyl groups including the just added dimethicone copolyol and the unreacted polysorbate groups present from the beginning. The polyesters are complicated mixtures of oligomers that are multiphillic polyesters. While not wanting to be bound by any one theory of operation, we believe that the block polymers that result have polysorbate, succinic DMC linkages in which the lowest free energy from aqueous solution is one in which the fatty group on the polysorbate is orientated toward the substrate, the water soluble polysorbate polyoxyalkylene groups are orientated away from the substrate, and the silicone portion is orientated toward the substrate. This repeating pattern results in a "sewing together" of groups that are captured on the surface of the substrate. The result is a molecule that is "entangled" in the substrate, having the water soluble groups pointing out of the substrate. This results in enhanced durability and hydrophilic surface treatments. A self wetting, conditioner, providing durable softness results. These properties are highly prized in personal care applications including shampoos, body wash, and baby products. The improved hydrophilic properties makes substrates so treated water loving, a requirement for absorbent applications, and a rarity in products which have a lot of fatty or silicone content in the molecule.

DETAILED DESCRIPTION OF THE INVENTION

One aspect of the present invention is directed toward a polyester of the present invention made by the reaction of:
(a) dimethicone copolyol conforming to the following structure:

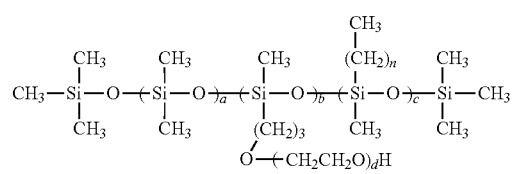

wherein:
a is an integer ranging from 0 to 200;
b is an integer ranging from 2 to 20;
c is an integer ranging from 0 to 10;
d is an integer ranging from 5 to 20;
n is an integer ranging from 7 to 17;
with succinic anhydride which conforms to the following structure:

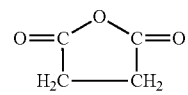

at a temperature of between 50 and 100° C., said the mole ratio of said succinic anhydride to hydroxyl group ranging from a value of b/2 to b/5 to producing a carboxyl ester having between half and one fifth of the hydroxyl groups esterified, one of said compounds conforming to the following structure when b=10 and half of the hydroxyl groups have been esterified:

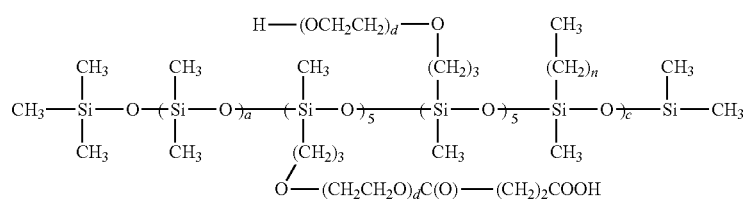

Another of said compounds conforming to the following structure when b=10 and one fifth of the hydroxyl groups have been esterified:

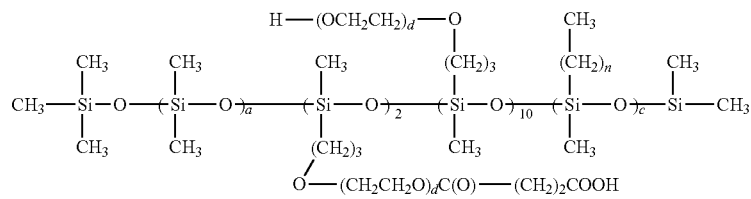

followed by reaction of the intermediate with a polysorbate conforming to the following structure;

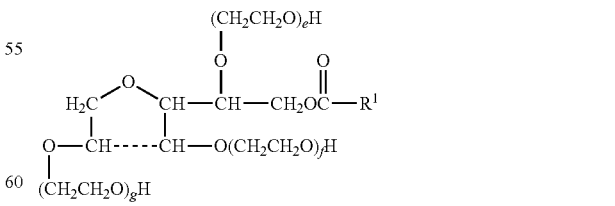

e is an integer ranging from 0 to 30;
f is an integer ranging from 0 to 30;
g is an integer ranging from 0 to 30, with the proviso that e+f+g is an integer ranging from 9 to 50;
$R^1$ is alkyl having from 7 to 21 carbon atoms;

wherein the ratio of hydroxyl on the polysorbate to carboxyl group ranges from 4:1 to 2:1.

The remaining hydroxyl groups react with the carboxyl groups of the polysorbate and those of the dimethicone to make a random polymer. It will be appreciated that when the succinic anhydride to hydroxyl ratio on the dimethicone copolyol are high, few hydroxyl groups are left on the dimethicone copolyol and consequently the hydroxyl groups on the polysorbate react. This offers outstanding ability to control the pattern of the resulting polymer.

A polyester results in which there is always a succinate group between the polysorbate and dimethicone copolyol, but the arrangement of polysorbate and dimethicone copolyol units relative to each other is determined by mole ratio of DMC to succinate in step one and hydroxyl in the polysorbate to carboxyl in the intermediate.

A-B-C-B-A-B-A-C-A-B-A wherein

A is dimethicone copolyol

B is —C(O)—CH$_2$CH$_2$—C(O)—

C is polysorbate

Another aspect of the present invention is a process for conditioning fiber, which comprised contacting the fiber with an effective conditioning concentration of a polyester made by the reaction of:

(a) dimethicone copolyol conforming to the following structure:

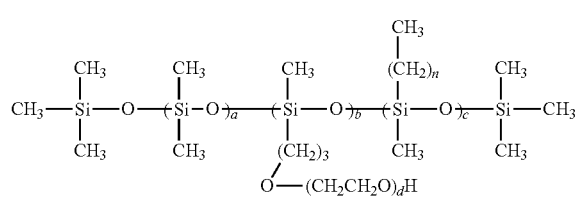

wherein:

a is an integer ranging from 0 to 200;

b is an integer ranging from 2 to 20;

c is an integer ranging from 0 to 10;

d is an integer ranging from 5 to 20;

n is an integer ranging from 7 to 17;

with succinic anhydride which conforms to the following structure:

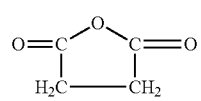

at a temperature of between 50 and 100° C., said the mole ratio of said succinic anhydride to hydroxyl group ranging from a value of b/2 to b/5 to producing a carboxyl ester followed by reaction of the intermediate with a polysorbate conforming to the following structure;

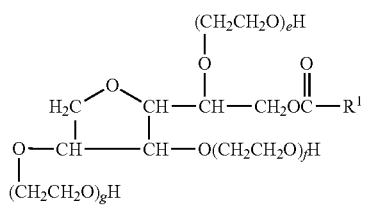

e is an integer ranging from 0 to 30;

f is an integer ranging from 0 to 30;

g is an integer ranging from 0 to 30, with the proviso that e+f+g is an integer ranging from 9 to 50;

R$^1$ is alkyl having from 7 to 21 carbon atoms;

with said carboxyl ester wherein the ratio of hydroxyl on the polysorbate to carboxyl group ranges from 4:1 to 2:1.

In a preferred embodiment the process is carried out using an effective conditioning concentration ranges from 0.1 to 15% by weight.

Preferred Embodiments

The presence of polyoxyethylene groups —(CH$_2$CH$_2$—O)$_x$H on both the polysorbate and dimethicone copolyol affects water solubility. In a preferred embodiment where the products are water-soluble the percent polyoxyethylene groups in the molecule ranges from between 40 and 65 percent of the total molecular weight of the polymer.

In a preferred embodiment, the dimethicone copolyol compounds of the present invention contain alkyl groups.

In a preferred embodiment the alkyl groups have between 12 and 14 carbon atoms.

In a preferred embodiment e+f+g is an integer ranging from 18 to 25.

In a preferred embodiment e+f+g equals 20.

In a preferred embodiment said fiber is hair.

In a preferred embodiment said fiber is textile fiber.

In a preferred embodiment said fiber is paper.

In a preferred embodiment said effective concentration ranges from 0.1 to 15% by weight.

In a more preferred embodiment said effective concentration ranges from 1 to 10% by weight.

In a still more preferred embodiment said effective concentration ranges from 1 to 8% by weight Examples Raw Materials A. Dimethicone Copolyol By dimethicone copolyol compounds is meant compounds in which there are at least two water soluble groups (the "b" segment), at least two "D" units (the "a" segment) and in a preferred embodiment an alkyl group (the "c" segment). Dimethicone copolyol compounds are items of commerce available from Siltech LLC, Dacula, Ga. which conform to the following structure:

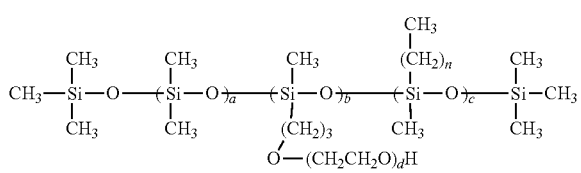

wherein:
a is an integer ranging from 0 to 200;
b is an integer ranging from 2 to 20;
c is an integer ranging from 0 to 10;
d is an integer ranging from 5 to 20;
n is an integer ranging from 7 to 17.

Examples

| Example | a | b | c | d | n |
|---|---|---|---|---|---|
| 1 | 0 | 2 | 0 | 5 | — |
| 2 | 10 | 4 | 2 | 12 | 11 |
| 3 | 20 | 12 | 10 | 10 | 7 |
| 4 | 30 | 20 | 6 | 20 | 11 |
| 5 | 50 | 10 | 0 | 10 | — |
| 6 | 200 | 20 | 2 | 8 | 13 |
| 7 | 10 | 4 | 0 | 8 | — |

2. Polysorbates

Polysorbates are compounds of commerce, available from a variety of sources including Croda. They conform to the following structure:

$e$ is an integer ranging from 0 to 30;
$f$ is an integer ranging from 0 to 30;
$g$ is an integer ranging from 0 to 30, with the proviso that $e+f+g$ is an integer ranging from 9 to 50;
$R^1$ is alkyl having from 7 to 21 carbon atoms;

| Example | e | f | g | e + f + g | $R^1$ |
|---|---|---|---|---|---|
| 8 | 3 | 3 | 3 | 9 | C11 |
| 9 | 7 | 7 | 7 | 21 | C15 |
| 10 | 7 | 7 | 7 | 21 | C17 |
| 11 | 7 | 7 | 7 | 21 | C21 |
| 12 | 10 | 10 | 10 | 30 | C11 |
| 13 | 8 | 8 | 8 | 24 | C11 |
| 14 | 17 | 16 | 17 | 50 | C11 |

3. Crosslinking Anhydride

Succinic Anhydride

As should become obvious, the nature of the succinic anhydride makes possible the two-step reaction used to make the product of the present invention. The key to its effectiveness is the fact that the anhydride will open up to form a carboxy acid at low temperatures, producing essentially no diester, allowing the option to run second reaction at the carboxyl end with a different hydroxyl containing material. This regiospecificity is a very important factor in making products of the present invention. Attempting to make the product in one step results in diester in step one and a gel that does not allow for subsequent reaction.

Succinic Anhydride conforms to the following structure;

General Procedure—Reaction Sequence 1

Preparation of the Dimethicone Copolyol Succinate Half Ester.

To the specified number of grams of the specified dimethicone copolyol (Examples 1-7) is added 100 grams of succinic anhydride. The reaction mass is heated to 100° C., care is exercised not to exceed 110° C. to minimize diester formation. The reaction proceeds as the acid value reaches theoretical. The reaction is ready for reaction sequence step 2.

Dimethicone Copolyol

| Example | Example | Grams | % OH Consumed | mole ratio of succinic anhydride to hydroxyl |
|---|---|---|---|---|
| 15 | 1 | 380 | 50 | b/2 |
| 16 | 2 | 2160 | 20 | b/5 |
| 17 | 3 | 1210 | 20 | b/5 |
| 18 | 4 | 472 | 50 | b/2 |
| 19 | 5 | 2440 | 20 | b/5 |
| 20 | 6 | 2520 | 33 | b/3 |
| 21 | 7 | 1745 | 20 | b/5 |

Compounds of the Present Invention

General Procedure—Reaction Sequence Step 2

Preparation of Polyester.

To the examples above (Examples 15-21) is added the specified number of grams of the specified polysorbate (Examples 8-14). The reaction mass is heated to 180° C. The reaction proceeds as water is distilled off and the acid value becomes vanishingly small. The reaction is cooled and used as is in reaction sequence 2.

Step 1 Product

| Example | Example | Grams | Example | Grams | Polysorbate hydroxyl to carboxyl ratio |
|---|---|---|---|---|---|
| 22 | 15 | 480 | 8 | 908 | 4:1 |
| 23 | 16 | 2260 | 9 | 766 | 2:1 |
| 24 | 17 | 1310 | 10 | 1724 | 4:1 |
| 25 | 18 | 572 | 11 | 1350 | 3:1 |
| 26 | 19 | 2540 | 12 | 2140 | 4:1 |
| 27 | 20 | 2620 | 13 | 894 | 2:1 |
| 28 | 21 | 1845 | 14 | 2505 | 3:1 |
| 29 | 21 | 1845 | 11 | 1800 | 4:1 |

Application Examples

Wetting

Draves Wetting

Draves Wetting measures the length of time needed to sink a cotton skein (which is very similar to a hair tress) in an aqueous solution (the faster the time, the better the wetting). In the Draves Wetting test, a 0.5% solution of dimethicone copolyol is used to sink a cotton skein. The reported values are on a scale of 1 to 5, with 1 being almost immediate and 5 being over 5 minutes.

Conditioning/Combability

The following test was performed to determine the conditioning and combability properties.

DeMeo Brothers. Five two-gram tresses were used per product evaluated. All tresses were pre-washed three times with Prell® original shampoo, rinsed in water at 25° C., and air-dried. The test scale was:

1=Very poor 2=Poor 3=Satisfactory 4=Good 5=Excellent

Antistatic Properties

The hair treated in the conditioning study was combed 50 times. The resulting hair was then evaluated for static build up. The test scale was:

1=Very poor 2=Poor 3=Satisfactory 4=Good 5=Excellent

Re-Wet

When softening agents are used to treat textile fibers; they make the substrate soft but do some the hydrophobic. What this means is that the substrate is soft to the feel, but does not absorb water. The reason for this is that the softness is due to oil loving materials deposited on the substrate. We have all encountered soft towels that fail to absorb water. It is critical to many applications for the substrate to be both soft and re-wet. Hair that fails to rewet is referred to as "gunky" and is cosmetically unacceptable.

In order to evaluate re-wet, we apply a 1% solution of the test material to a paper towel in a test area per-marked with a pencil. We then allow it to air dry. After drying we apply one drop of water. The time it takes to spread is evaluated on a scale of 1 to 5. The test scale was: 1=Very poor 2=Poor 3=Satisfactory 4=Good 5=Excellent

|  | Properties | | | |
| --- | --- | --- | --- | --- |
| Compounds of the Invention | Softness | Antistatic | Wetting | Rewet |
| Example 28 | 4 | 4 | 3 | 5 |
| Example 29 | 4 | 3 | 4 | 4 |
| Example 23 | 4 | 5 | 3 | 4 |

|  | Properties | | | |
| --- | --- | --- | --- | --- |
| Comparative Compounds | Softness | Antistatic | Wetting | Rewet |
| Polysorbate Example 11 | 1 | 2 | 3 | 3 |
| Dimethicone Copoylol | 1 | 2 | 2 | 3 |
| Stearalkonium Chloride | 4 | 3 | 1 | 1 |

As can easily be seen the compounds of the present invention have improved properties, which are highly desirable in a variety of applications.

While the illustrative embodiments of the invention have been described with particularity, it will be understood that various other modifications will be apparent to and can be readily made by those skilled in the art without departing from the spirit and scope of the invention. Accordingly, it is not intended that the scope of the claims appended hereto be limited to the examples and descriptions set forth hereinabove but rather that the claims be construed as encompassing all the features of patentable novelty which reside in the present invention, including all features which would be treated as equivalents thereof by those skilled in the art to which the invention pertains.

The invention claimed is:

1. A polyester made by the reaction of
(a) dimethicone copolyol conforming to the following structure:

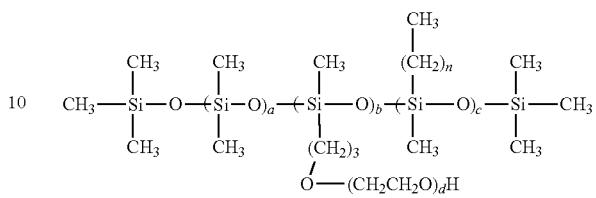

wherein;
a is an integer ranging from 0 to 200;
b is an integer ranging from 2 to 20;
c is an integer ranging from 0 to 10;
d is an integer ranging from 5 to 20;
n is an integer ranging from 7 to 17;
with succinic anhydride which conforms to the following structure:

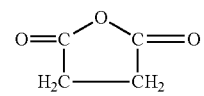

at a temperature of between 50 and 100° C., wherein the mole ratio of said succinic anhydride to hydroxyl group ranges from a value of b/2 to b/5 to producing a carboxyl ester;
followed by reaction of the intermediate with a polysorbate conforming to the following structure;

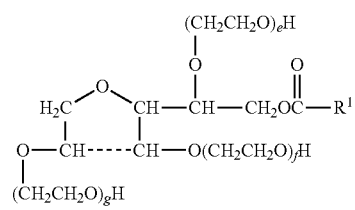

e is an integer ranging from 0 to 30;
f is an integer ranging from 0 to 30;
g is an integer ranging from 0 to 30, with the proviso that e+f+g is an integer ranging from 9 to 50;
$R^1$ is alkyl having from 7 to 21 carbon atoms;
with said carboxyl ester
wherein the ratio of hydroxyl on the polysorbate to carboxyl group ranges from 4:1 to 2:1.

2. A polyester of claim 1 wherein a is an integer ranging from 1 to 20.

3. A polyester of claim 1 wherein b is an integer ranging from 2 to 10.

4. A polyester of claim 1 wherein c is 0.

5. A polyester of claim 1 wherein c is integer ranging from 1 to 5.

6. A polyester of claim 1 wherein e+f+g is an integer ranging from 15 to 30.

7. A process for conditioning fiber which comprised contacting the fiber with an effective conditioning concentration of a polyester made by the reaction of (b) dimethicone copolyol conforming to the following structure:

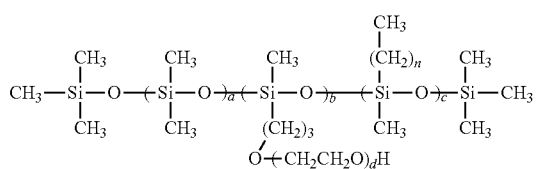

wherein:
a is an integer ranging from 0 to 200;
b is an integer ranging from 2 to 20;
c is an integer ranging from 0 to 10;
d is an integer ranging from 5 to 20;
n is an integer ranging from 7 to 17;
with succinic anhydride which conforms to the following structure:

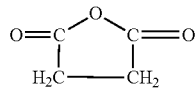

at a temperature of between 50 and 100° C., wherein the mole ratio of said succinic anhydride to hydroxyl group ranges from a value of b/2 to b/5 to producing a carboxyl ester;
followed by reaction of the intermediate with a polysorbate conforming to the following structure;

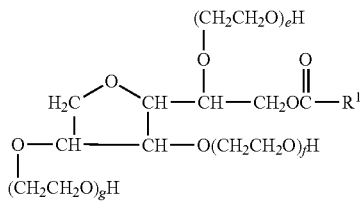

e is an integer ranging from 0 to 30;
f is an integer ranging from 0 to 30;
g is an integer ranging from 0 to 30, with the proviso that e+f+g is an integer ranging from 9 to 50;
$R^1$ is alkyl having from 7 to 21 carbon atoms;
with said carboxyl ester
wherein the ratio of hydroxyl on the polysorbate to carboxyl group ranges from 4:1 to 2:1.

8. A process of claim 7 wherein said fiber is hair.

9. A process of claim 7 wherein said fiber is textile fiber.

10. A process of claim 7 wherein said fiber is paper.

11. A process of claim 7 wherein said effective concentration ranges from 0.1 to 15% by weight.

12. A process of claim 7 wherein a is an integer ranging from 1 to 20.

13. A process of claim 7 wherein b is an integer ranging from 2 to 10.

14. A process of claim 7 wherein c is 0.

15. A process of claim 7 wherein c is integer ranging from 1 to 5.

16. A process of claim 7 wherein e+f+g is an integer ranging from 15 to 30.

* * * * *